(12) United States Patent
Ito et al.

(10) Patent No.: US 6,174,734 B1
(45) Date of Patent: *Jan. 16, 2001

(54) MEASUREMENT OF GLYCATED HEMOGLOBIN

(75) Inventors: Ralph K. Ito, Hopkinton; Gordon Sanghera, Newton, both of MA (US)

(73) Assignee: Abbott Laboratories, Abbott Park, IL (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/957,104

(22) Filed: Oct. 24, 1997

(51) Int. Cl.$^7$ .................................................. G01N 33/543
(52) U.S. Cl. ........................... 436/518; 435/7.1; 436/66; 436/67; 436/522; 436/524; 436/531; 436/534; 436/805
(58) Field of Search ................................ 435/7.1; 436/66, 436/67, 518, 522, 524, 431, 534, 805

(56) References Cited

U.S. PATENT DOCUMENTS

| | | |
|---|---|---|
| 4,268,270 | 5/1981 | Gabbay et al. . |
| 4,269,605 | 5/1981 | Dean et al. . |
| 4,438,204 | 3/1984 | Deeg et al. . |
| 4,478,744 | 10/1984 | Mezei et al. . |
| 4,496,722 | 1/1985 | Gallop et al. . |
| 4,647,654 | 3/1987 | Knowles et al. . |
| 4,695,552 | 9/1987 | Schmitt et al. . |
| 4,727,036 | 2/1988 | Knowles et al. . |
| 4,800,167 * | 1/1989 | Bailey et al. ........................... 436/66 |
| 4,806,468 * | 2/1989 | Wagner et al. ......................... 435/28 |
| 4,847,209 * | 7/1989 | Lewis et al. .......................... 436/533 |
| 4,861,728 * | 8/1989 | Wagner et al. ........................ 436/501 |
| 5,252,459 | 10/1993 | Tarcha et al. . |
| 5,459,080 | 10/1995 | Adamczyk et al. . |
| 5,478,754 | 12/1995 | Brandt et al. . |
| 5,686,316 * | 11/1997 | Fiechtner et al. ..................... 436/518 |

FOREIGN PATENT DOCUMENTS

| | | |
|---|---|---|
| 0407860 | 1/1991 | (EP) . |
| 0 573 972 | 12/1993 | (EP) . |
| 0745843 | 4/1996 | (EP) . |
| 0 864 865 | 9/1998 | (EP) . |
| 92/08984 | 5/1992 | (WO) . |
| 9639180 | 12/1996 | (WO) . |

OTHER PUBLICATIONS

Abbas et al., "Immunologic tolerance and the regulation of immune responses", *Cellular and Molecular Immunology*, W. B. Saunders Company, Philadelphia, PA, pp. 205–221.
Adam et al., "Immunoadjuvants", *Structure of Antigens*, Van Regenmortel, ed., CRC Press, Inc., (1992), pp. 159–177.
Butler, *Immunochemistry of Solid–Phase Immunoassay*, CRC Press, Boca Raton, FL, 1991.
Goding, "Production of monoclonal antibodies", *Monoclonal Antibodies: Principles and Practice*, Academic Press, London, 1996, pp. 141–233.
Goldstein et al., "Glycated hemoglobin: Methodologies and clinical applications", *Clinical Chemistry*, vol. 32 (1986), pp. B64–B70.
Goldstein, "How much do you know about glycated hemoglobin", *Clinical Diabetes*, (1995), pp. 60–64.

(List continued on next page.)

Primary Examiner—Christopher L. Chin
(74) Attorney, Agent, or Firm—David L. Weinstein; Lawrence S. Pope (57) ABSTRACT

The invention features a novel method of assaying glycated hemoglobin (GHb) in a sample using a capture molecule that binds GHb and hemoglobin (Hb), and detecting bound GHb with a molecule that distinguishes GHb from non-glycated hemoglobin (Hb). The molecule used to distinguish GHb from Hb may be an antibody. The assay and antibodies of the invention are useful for the evaluation of GHb in disease states such as diabetes.

7 Claims, 4 Drawing Sheets-

OTHER PUBLICATIONS

Greer, "Model for haptoglobin heavy chain based upon structural homology", *Proc. Natl. Acad. Sci. USA*, vol. 77, (1980) pp. 3393–3397.

Greer, "Haptoglobin–hemoglobin complex", *The Journal of Biological Chemistry*, vol. 256 (1981), pp.8771–8774.

Groves et al., "The Production and application of non–rodent monoclonal antibodies in veterinary science", *Veterinary Immunology and Immunopatholoby*, vol. 23 (1989), pp. 1–14.

Harlow et al., "Immunizations", *Antibodies A Laboratory Manual*, Cold Spring Harbor Laboratory, (1988), pp.53–137.

Hwang et al., "Interaction between hemoglobin subunits in the hemoglobin haptoglobin complex", *The Journal of Biological Chemistry*, vol. 255 (1980), pp. 3038–3041.

Langlois et al., "Biological and clinical significance of haptoglobin polymorphism in humans", *Clinical Chemistry*, vol. 42 (1996), pp. 1589–1600.

Lustbader, et al., "Hemoglobin–binding site on haptoglobin probed by selective proteolysis", *The Journal of Biological Chemistry*, vol. 258 (1983), pp. 1227–1234.

Makinen, et al., "Specificity of interaction of haptoglobin with mammalian hemoglobin", *Biochemistry*, vol. 11 (1972), pp. 3851–3860.

McCormick et al., "Hemoglobin binding with haptoglobin: Delineation of the haptoglobin binding site on the α–chain of human hemoglobin", *Journal of Protein Chemistry*, vol. 9 (1990), pp. 735–742.

McNeil et al., "Immunosensors for clinical diagnostics", *Frontiers in Biosensorics II, Practical Application*, Scheller et al., eds., Birkhäuser Verlag, Basel (1997), pp. 17–25.

Nagel et al., "The binding of hemoglobin to haptoglobin and its relation to subunit dissociation of hemoglobin", *The Journal of Biological Chemistry*, vol. 246 (1971), pp. 69–73.

Ou et al., "Comparison of two techniques for targeting the production of monoclonal antibodies against particular antigens", *Journal of Immunological Methods*, vol. 145 (1991), pp. 111–118.

Singer et al., "Tests of glycemia in diabetes mellitus", *Annals of Internal Medicine*, vol. 110 (1989), pp. 125–137.

Stewart–Tull et al., "The Theory And Practical Application Of Adjuvants", John Wiley & Sons, Chichester, England (1995).

Valette et al., "Haptoglobin heavy and light chains", *The Journal of Biological Chemistry*, vol. 256 (1981), pp. 672–679.

Wejman et al., "Strucutre of Haptoglobin and the haptoglobin–hemoglobin complex by electron microscopy", *Journal of Molecular Biology*, vol. 174 (1984), pp. 319–341.

Yoshioka et al., "Haemoglobin binding with haptoglobin", *Biochem. J.*, vol. 234 (1986), pp. 453–456.

\* cited by examiner

MEASUREMENT OF GLYCATED HEMOGLOBIN

FIELD OF THE INVENTION

The invention relates to hemoglobin, immunology, and blood analysis.

BACKGROUND OF THE INVENTION

In the presence of glucose, hemoglobin (Hb) is glycated by a nonenzymatic reaction stabilized by an Amadori rearrangement. Potential glycation sites are the N-terminal amino acids of the four polypeptide chains, and free $\epsilon$-amino groups of lysine within the chains. The most reactive site, HbA1c, is the N-terminal valine of the $\beta$chain, which accounts for about 60% of all bound glucose. Bound sugars can also appear at any of 44 glycation sites on the $\epsilon$-amino groups within the chains (about 34% of clycations), and the N-terminus of the a-chains (about 6% of glycations). The rate of glycation at any one site is directly proportional to glycation at any other site. Therefore, there is a linear relationship between the total amount of glycated hemoglobin (GHb) and any particular form of glycated hemoglobin (e.g., HbA1c).

A determination of the level of GHb in an individual can serve as an index of the blood glucose levels in the blood over time. The measurement of GHb) in diabetics is a useful indicator of disease state. Because the average blood cell has a lifespan of 120 days, (GHb levels reflect the blood glucose history of an individual over several months (Singer, *Ann. Intern. Med.*, 1989, 110:125-137), with most recent blood glucose levels being most strongly represented. It is recommended that diabetes be monitored by determining levels of GHb every 2–3 months to determine the progress of disease, the efficacy of control of the disease, or both.

Many methods for assessing GHb concentrations require separation of GHb from Hb. One type of separation method is based on the charge difference between GHb and Hb. This can be done, for example, by electrophoresis, high performance liquid chromatography (HPLC), or conventional ion exchange chromatography. Structural differences have also been exploited in assays of GHb, using methods such as affinity binding, chromatography, and immunoassay (Goldstein et al., *Clin. Chem.*, 1996, 32/10B, B64–B70).

Antibodies that have limited specificity for native HbA1c have been obtained by using glycosylated synthetic peptide sequences from the N-terminal region of the Hb $\beta$-chain (Knowles, U.S. Pat. Nos. 4,647,654 and 4,727,036; Mezei, U.S. Pat. No. 4,478,744). These antibodies have significantly less affinity for native HbA1c compared to the peptides against which they were raised. Because the antigenic site is difficult to access in native HbA1c, methods to denature HbA1c (Lewis, EP 401 860 A2; Knowles U.S. Pat. No. 4,727,036) have been used to develop immunoassays for HbA1c. Another approach is to degrade the Hb molecule with an enzyme, e.g., pepsin, to expose the N-terminal $\beta$-chain site. Methods for immunoassay of GHb generally employ denaturation or degradation pretreatment steps for antibody and/or assay development.

SUMMARY OF THE INVENTION

In general, the invention features a device and assay method for determining GHb in a biological fluid, antibodies useful in the device and assay method, and a method for producing such antibodies. The device and assay method are useful for the evaluation of GHb in disease states such as diabetes.

The invention features a device or kit for assaying GHb in a biological fluid. The device or kit includes a solid support member, which comprises a predetermined amount of an immobilized GHb/Hb capture molecule. Optionally, the device or kit includes a means of detecting a glycation probe that is specific for GHb, or an Hb/Hp-specific probe that is used to detect Hb bound to haptoglobin (Hp). The glycation probe can be, e.g., an antibody or a boronate derivative. The Hb/Hp-specific probe can be an antibody. The capture molecule can be haptoglobin or an antibody. The means for detecting the glycation probe can involve any suitable method, e.g., chemiluminescence, electrosensing, fluorimetry, fluorescence quenching, enzymatic immunocytochemistry, or visualization of particles.

The invention also features a method for detecting glycated hemoglobin in a biological fluid. The method includes the steps of: (a) providing a solid support member, which includes a predetermined amount of a GHb/Hb capture molecule, (b) contacting the biological fluid with the support member, thereby forming a GHb/Hb-saturated support member, (c) contacting the GHb/Hb-saturated support member with a glycation probe, (d) removing unbound glycation probe, and (e) detecting the glycation probe bound to captured GHb.

Glycated hemoglobin can also be assayed in a biological fluid by a method that includes the steps of: (a) providing a solid support member, which includes a predetermined amount of a GHb/Hb capture molecule, (b) contacting the biological fluid with the support member, thereby forming a GHb/Hb-saturated support member, contacting the GHb/Hb-saturated support member with an Hb/Hp-specific probe, (d) removing unbound Hb/Hp-specific probe, and (e) determining the amount of the Hb/Hb-specific probe bound to captured Hb, and calculating how much GHb is in the biological fluid, if present.

The glycation probe or Hb/Hp-specific probe can be labelled directly or detected indirectly, e.g., with an antibody. The glycation probe can specifically bind nondenatured GHb or GHb conformer H. The Hb/Hp-specific probe can specifically bind Hb or Hb conformer H. Preferably, the glycation probe specifically binds GHb conformer H. It is preferred that an Hb/Hp-specific probe bind Hb conformer H.

Preferably, the capture molecule is haptoglobin. Alternatively, it can be an antibody. The biological fluid is from a human or a nonhuman mammal. typically, the biological fluid is blood.

The invention also features a method for producing non-denatured GHb-specific or GHb conformer H-specific antibodies. The method includes the steps of: (a) binding GHb to haptoglobin (Hp), thereby producing a GHb/Hp complex, (b) placing the GHb/Hp complex into an antibody production system, (c) obtaining an antibody-containing product from the production system, and (d) detecting GHb or GHb conformer H-specific antibodies in the product.

The invention also features a method for producing Hb conformer H-specific antibodies. The method includes the steps of: (a) binding Hb to haptoglobin (Hp), thereby producing a Hb/Hp complex, (b) placing the Hb/Hp complex into an antibody production system, (c) obtaining an antibody-containing product from the production system, and (d) detecting Hb conformer H-specific antibodies in the product. The binding between GHb or Hb and Hp can be covalent or non-covalent. Hp may be from any mammal, preferably a human or a sheep. The antibody production system can be any nonhuman mammal, preferably a rabbit, a mouse, a rat, a goat, a chicken, a donkey, or a sheep. Alternatively, the antibody production system can be an in vitro system.

The invention also features an antibody produced by the methods described above, wherein the antibody selectively binds to nondenatured GHb, GHb conformer H, or Hb conformer H in the presence of Hb. For example, the antibody can display any of the following binding specificities: (a) nondenatured GHb, (b) GHb conformer H, (c) nondenatured GHb and GHb conformer H, (d) nondenatured Hb, (e) Hb conformer H, and (f) nondenatured Hb and Hb conformer H. Preferably the antibody specifically binds nondenatured GHb, GHb conformer H, or both.

As used herein, "hemoglobin" (Hb) means all naturally occurring forms of non-glycated hemoglobin, including tetrameric forms of $\alpha\alpha\beta\beta$ top and dimeric forms, e.g., $\alpha\beta$, and disease variants that bind to capture molecules.

As used herein, "glycated hemoglobin" (GHb) means hemoglobin having covalently attached sugar moieties (e.g., HbA1c) and GHb formed through a non-enzymatic reaction via an Amadori rearrangement.

As used herein, "hemoglobin conformer H" (Hb conformer H) means a hemoglobin in a non-native conformation inducible by a haptoglobin binding event.

As used herein, "glycated hemoglobin conformer H" (GHb conformer H) means a glycated hemoglobin in a non-native conformation inducible by a haptoglobin binding event.

As used herein, "haptoglobin" means all configurations of the haptoglobin heavy and light chains, including naturally occurring forms 1-1, 2-1, and 2-2.

As used herein, "capture molecule" means a molecule that binds glycated and non-glycated forms of hemoglobin with approximately equal affinity.

As used herein, "glycation probe" means a probe that binds specifically to glycated Hb. The glycated Hb can be unbound or bound to a capture molecule.

As used herein, "Hb/Hp-specific p)robe" means a probe that specifically binds to Hb bound to a capture molecule.

As used herein, an "antibody production system" means a living animal or in vitro system.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1A:
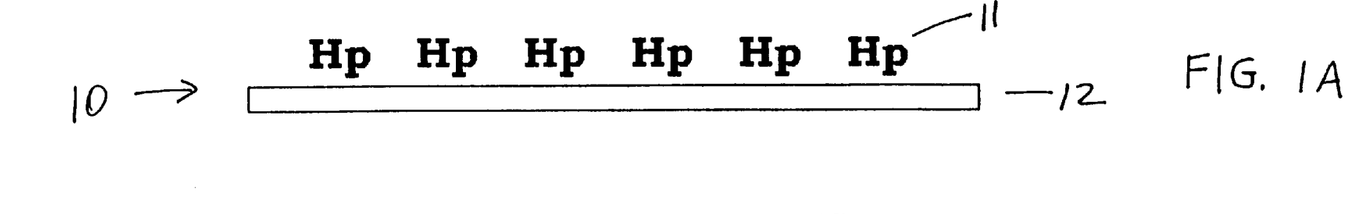
FIG. 1A depicts a solid support comprising a capture molecule.
Figure 1B:
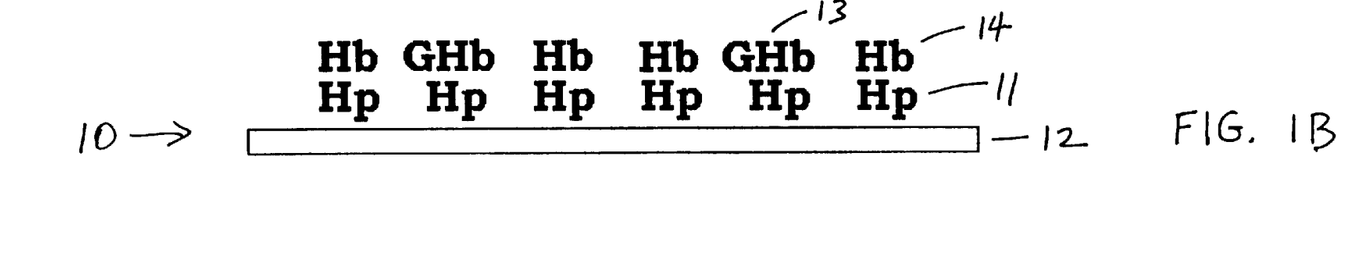
FIG. 1B depicts a solid support comprising a capture molecule bound to GHb and Hb.
Figure 1C:
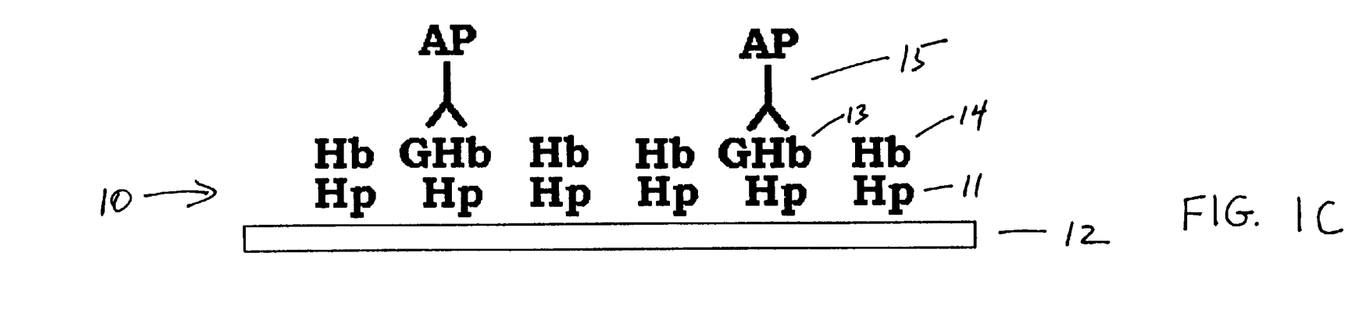
FIG. 1C depicts a solid support comprising a capture molecule bound to GHb and Hb, and a glycation probe.

A device and its operation in accordance with the invention is illustrated schematically in FIGS. 1A–1C. FIG. 1A depicts a capture field 10 comprising a solid support 12 and a predetermined amount of Hp 11 immobilized on the solid support. FIG. 1B illustrates a GHb 13/Hb 14-saturated capture field 10, i.e. with all of its capture sites occupied. In FIG. 1B excess (unbound) GHb and Hb have been removed. FIG. 1C represents a saturated capture field with alkaline phosphatase (AP)-conjugated, GHb-specific antibody 15, bound to GHb. In FIG. 1C unbound antibody has been removed. When the AP substrate, p-amino phenyl phosphate (pAPP), is contacted with the saturated, antibody-treated capture field, the enzyme (AP) generates the product p-amino phenol (pAP). The rate of pAP formation, or the quantity of pAP formed, is measured electrochemically. The amount of GHb in the sample is proportional to the rate or quantity of pAP, and is related to a standard curve. Thus, the relative amount of GHb is determined.

The capture molecule binds GHb and Hb with similar affinity, therefore it binds GHb and Hb in a ratio reflecting their relative concentrations in the sample. The total amount of Hp in the capture field is predetermined. Therefore the total amount of captured GHb/Hb is known. The relative amount of GHb in the sample is calculated using the absolute amount of GHb (determined as described above) and the known amount of captured GHb/Hb.

In a similar device, an Hb/Hp-specific probe is used instead of a glycation probe. In this case, Hb bound to the capture field is detected with the Hb/Hp-specific probe. The relative amount of GHb present in the sample is calculated by subtracting the amount of Hb bound to the capture field from the total number of binding sites in the capture field.

Elements of a device such as that described above can be supplied separately, thus constituting a kit.

Figure 2:
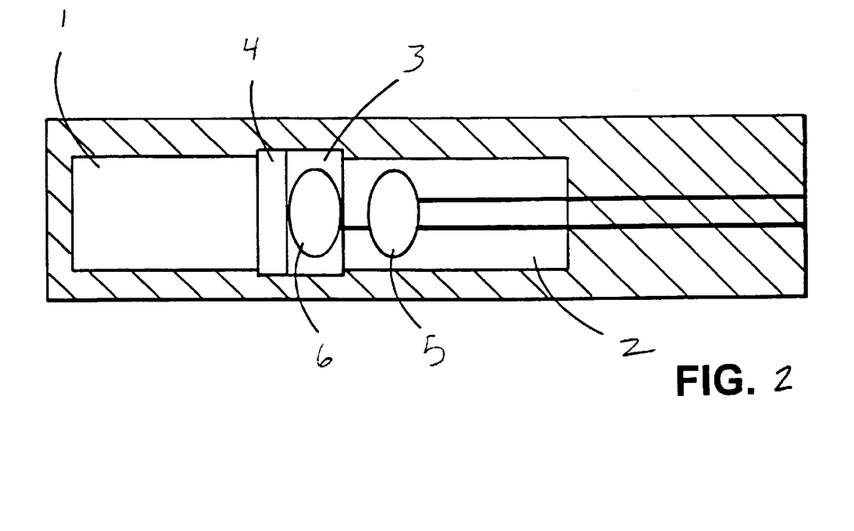
FIG. 2 is a top view of an assay device that illustrates the invention.
Figure 3:
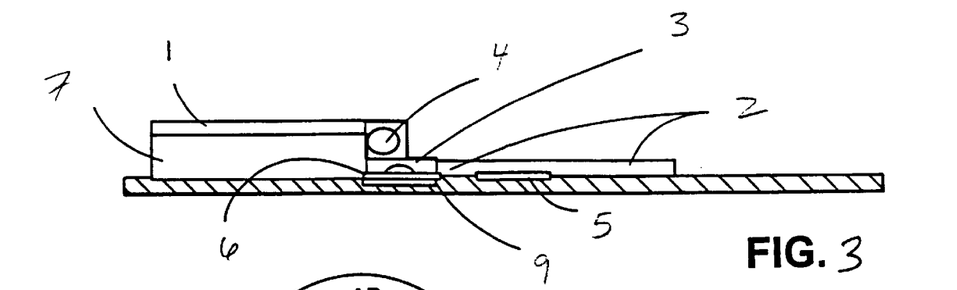
FIG. 3 is a side view of the assay device depicted in FIG. 1.
Figure 4:
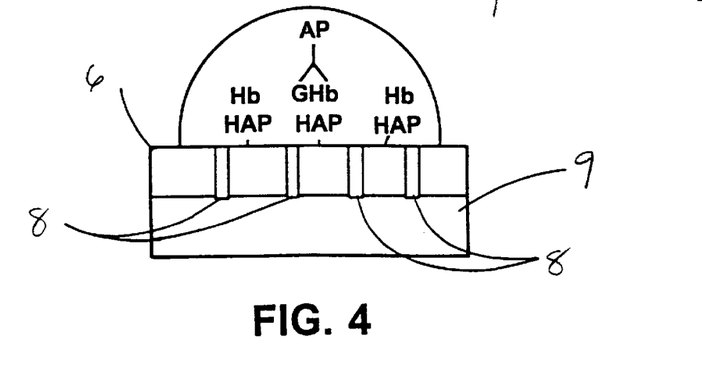
FIG. 4 is a cross-sectional detail of the capture/detection portion of the invention.

An example of another device according to the invention is illustrated in FIGS. 2–4. The device includes a sample wick 1, a draw wick 2, haptoglobin cover mesh 3, an antibody mesh 4, a dummy 5, and a sensor 6. A predetermined quantity of haptoglobin is immobilized on the sensor 6. Referring to FIG. 3, the sample wick 1 Lies on a support 7. When sample is applied to the sample/lysis wick 1, it diffuses through the antibody mesh 4 and continues through the haptoglobin cover mesh 3. The immobilized Hp on the sensor 6 binds the Hb and GHb with about equal affinity, thus, the bound GHb represents the percentage of GHb in the sample. The antibody specific for GHb:Hp complex and conjugated to AP is bound to the immobilized GHb:Hp complex. Sample is drawn through the meshes until the draw wick 2 is saturated which then stops fluid flow. Pores 8 in the sensor 6, allow the alkaline phosphatase substrate (pAPP) 9 to solubilize and migrate to the surface of the sensor where it interacts with the enzyme conjugate producing a detectable product. The dummy 5 comprises an antibody mesh as in 4 and a sensing electrode as in the sensor 6. The dummy does not have immobilized Hp associated with it. Its purpose is to provide a measure of background noise in the assay. Noise is thus subtracted from the signal generated at the sensor to achieve the final assay measurement. In general, the antibody used to detect GHb in this device has a greater affinity for GHb:Hp complex than for GHb alone. Therefore, the antibody does not preferentially bind to GHb (or Hb) in solution, but binds after GHb binds to Hp to form a complex. In the case where the antibody used to detect GHb has a greater or equal affinity for GHb compared to GHb:Hp complex, a larger amount of antibody is used in the device. The amount of antibody to be used is determined empirically by methods known to those in the art.

Sample Preparation

A relatively small amount of sample (e.g., a biological fluid) is used in the assay. For example, from about 1 $\mu$l to about 250 $\mu$l of whole blood is used in a single test.

Samples may be used immediately after collection or stored, preferably under refrigeration before use. Blood may also be anticoagulated, containing agents such as EDTA, heparin, or sodium citrate.

Blood samples may be hemolyzed and diluted for use in the invention. This can be done by a variety of methods, for example, by suspension in water or in an aqueous solution containing a non-ionic detergent (e.g., TRITON® X-100 detergent).

Solid Support and Capture Molecule

The solid support used to form the capture field can be in various geometries or formats, for example, membranes, beads, microparticles, magnetic microparticles, microtiter plates, latex-coated particles, or tubes. The support can be made of various materials, for example, nitrocellulose, nylon, polystyrene, polysulfone, polyacrylamide, agarose, dextran, latex, silica, plastics, or glass. The support material may be derivitized to include functional groups useful for attaching (e.g., by covalent bonds) the capture molecule. Such functional groups include, but are not limited to, aldehyde, aliphatic amine, aromatic amine, amide, carboxylic acid, sulfhydryl, chloromethyl, epoxy, hydrazide, and hydroxyl groups.

The capture molecule used in the assay can be haptoglobin or any other molecule that has the ability to bind GHb and Hb with a similar affinity (e.g., within two orders of magnitude, more preferably, within one order of magnitude).

Haptoglobin (Hp) is a naturally occurring plasma protein that specifically binds Hb and GHb. Hp contains two heavy chains (H) and two light chains (L) as a tetramer (Valette et al., 1981 *J. Biol. Chem.* 256:672-679). There are three major phenotypic forms of human Hp determined by two forms of the L chain, Hp1-1, Hp2-1, and Hp2-2 (Langlois and Delanghe, 1996 *Clin. Chem.* 42:1589-600). Hp binds hemoglobin during intravascular hemolysis as a mechanism to conserve iron and prevent renal damage by returning Hb to the liver.

Hb and GHb both include two $\alpha$ and two $\beta$ chains that can exist as a tetramer. Dimers of the chains are referred to as $\alpha_1\beta_1$ and $\alpha_2\beta_2$. The binding of Hp with Hb or GHb occurs between the H chain of Hp and a dimer of Hb (Greer et al., 1981 *J. Biol. Chem.* 256:8771-8774) or GHb. The amino acid regions on Hb or GHb that bind to Hp are $\beta$11-25, $\beta$131-146, and $\beta$121-127. The complex becomes an inflexible unit (Wejman et al., 1984. *J. Mol. Biol.* 174:319-341) and the conformational changes resulting from this interaction may enhance the immunogenicity of glycation sites.

Another example of a capture molecule is an antibody that recognizes GHb and Hb. An antibody that specifically binds the $\beta$-chain of Hb is preferred because it is less likely to interfere with recognition of the glycated sites of GHb (for example, Biodesign International, cat. no. H67696M).

The optimal form of Hp for use in this invention can be determined empirically by use of methods known in the art. The different forms of Hp are commercially available, for example, from Sigma (Hp 1-1, cat. no. H0138; Hp 2-1, cat. no. H9887; Hp 2-2, cat no. H9762).

Draw Wick

As shown in FIGS. 2–4, a sample to be assayed for GHb is drawn through the section of the device containing immobilized capture molecule by means of a draw wick. The wick may be made from a variety of materials including nylon, glass wool or fiber, cellulose paper, cotton, hydrogels, or plastics.

Glycation Probe and Hb/Hp-specific Probe

In this invention, the glycation probe can specifically bind nondenatured GHb, GHb conformer H, or both. Alternatively, the Hb/Hp-specific probe can be specific for Hb and Hb conformer H. The glycation probe or the Hb/Hp-specific probe can be an antibody. Suitable antibodies can be obtained as described in detail below. The glycation probe or Hb/Hp-specific probe can also be a molecule other than an antibody. For example, a boronate can serve as a glycation probe. Boronates (e.g., dihydroxyboronate) interact with sugar moieties of GHb, and may be linked to a detectable agent, as described in U.S. Pat. No. 4,269,605. Examples of boronate compounds are boronic, phenylboronic, boric acid, and boronate compounds or moieties. Additional boronate compounds that can be used in the invention are described in Gallop, U.S. Pat. No. 4,496,722. Boronates react with GHb via the cis-diol moiety of glucose bound to hemoglobin, forming a five-membered ring structure. Methods for labeling boronates are known in the art (e.g., U.S. Pat. No. 5,459,080).

The glycation probe or Hb/Hp-specific probe can be carried on a mesh or pad. The mesh or pad may be constructed from a variety of materials, including nylon, cellulose, nitrocellulose, paper, polyesters, polysulfones, glass wool, or fiber. Glycation probes and Hb/Hp-specific probes are not covalently attached to the mesh or pad. For example after soaking the mesh or pad in a solution containing the detecting molecule, the mesh is dried and sufficient probe adheres to the dried mesh to be useful in the device. The probe may also be drop-coated or spray-coated (i.e., ink jet spray) onto the mesh or pad, or onto a support.

Detection of Glycation Probe or Hb/Hp-specific Probe

GHb or Hb bound to a capture molecule is detected by a glycation probe or Hb/Hp-specific probe, respectively. The bound glycation probe or Hb/Hp-specific probe is then detected by direct or indirect methods. For direct visualization, a fluorescent label (e.g., fluorescein isothiocyanate, rhodamine, Texas red, or Cy3) can be covalently attached to the probe. For indirect detection, a second, labeled molecule (e.g., antibody) is applied to the sample in a "sandwich" technique. Methods for labeling antibodies and detecting such antibodies are known in the art. For example, see Coligan et al., *Cuirrent Protocols in Immunology*, John Wiley & Sons, 1994.

Detection can also be by means of a covalently attached enzyme e.g., alkaline phosphatase). Enzymatic labels typically require provision of a substrate. The substrate interacts with the enzyme to produce a detectable product. An inactivation step may be required to terminate the reaction. Methods used for this inactivation step can be washing with water, appropriate buffers, or addition of a chemical inactivating agent.

Other methods useful for detection of a probe include electrochemical detection (EP 0745843A2; McNeil et al., In: *Frontiers in Biosensorics II, Practical Applications*, Scheller et al., eds., pp.17–25, Birkhauser Verlag, Basel, 1997) detection of radioactive decay, and fluorescence quenching methods. Particle labels may also be used such as colloidal gold, latex beads, or polypyrolle. Such methods are known in the art (see, for example, U.S. Pat. No. 5,252,459; Oliver, In: Methocds in *Molecular aBiology*, vol. 34, Javois, ed., pp. 299–307, Humana Press Inc., Totowa, N.J.) The specific method applied will depend on the type of label used.

Methods of Preparing Antibodies

GHb for antigen preparation can be obtained in various ways. In one method, highly glycosylated GHb is isolated from diabetic patients. In this approach, a boronate column can be used to collect GHb from blood. GHb used to obtain the antibodies of the invention can be HbA1c, a mixture of GHb forms, or isolated GHb variants besides HbA1c.

Isolated GHb or Hb can be mixed with Hp to form GHb:Hp or Hb:Hp complexes, which are used as antigen. The Hp can be from any mammal, preferably a human or a sheep. The complexes are separated from non-complexed components and used as immunogen as described below. For example, GHb is reacted with Hp1-1 to form a complex of approximately 150,000 daltons. The complex is separated from GHb (about 64,000 daltons) and unbound Hp (about 85,000 daltons) by size exclusion chromatography. Similarly, Hp 2-1 and Hp 2-2 may be used in place of Hp 1-1. Hp:GHb complexes are characterized by total protein analysis and spectral absorbance to determine the amount of GHb bound per mass protein.

If human Hp is used, it can be of the Hp1-1 subclass or other subclasses, e.g., 2-1, 2-2, or a mixture of subclasses. Various Hp subclasses are commercially available. Other methods of preparing immunogen may be used such as those described in WO 96/39180.

The binding of GHb and Hb to Hp is such a high affinity interaction, i.e., about $10^{-10}$ to $10^{-15}$, in the prior art, it has been called "irreversible" (Hwang et al., 1980, *J. Biol. Chem.* 255:3083-3041). Therefore, noncovalently bound Hp/Hb complexes can be used. Alternatively, the complexes can be covalently linked using methods known in the art. Without committing to any particular theory, the method of the invention should provide antibodies against GHb since although the glycated sites are likely to be in a configuration advantageous for their presentation as antigen, they are relatively far from the Hp binding sites. Therefore, while Hp binds Hb to form a relatively rigid configuration that exposes the HbA1c epitope, Hp is unlikely to interfere with the antigenicity of th(e glycation sites on Hb or GHb.

To enhance the cellular and humoxal immune response to GHb, the antigen can be co-administered to an animal with an adjuvant. The immunogen is prepared by forming an emulsion or mixture of the antigen with the adjuvant. A preferred adjuvant is Freund's adjuvant (DIFCO, Detroit, Mich.). However, selection of other adjuvants (Stewart-Tull, The Theory and Practical Application of Adjuvants, 1995, Wiley, Chichester; Adam and Souvannavong, Structure of Antigens, CRC Press, Boca Raton, Fla., pp.159–177) such as, but not limited to, various RIBI Immunochem products (Hamilton Mont.), Titermax (Norcross, Ga.), Gerbu (Gaiberg, Germany), or alum mixtures is acceptable.

To further enhance antibody recognition of the antigen, immune response modulators (Hailow and Lane, 1988, *Antibodies: A Laboratory Manual*, Cold spring Harbor Laboratory, New York, pp.53–137) may be used with the immunogen or administered to the animal separately. This includes, but is not limited to, native or synthetic constituents of bacterial cell walls such as lipopolysaccharides (LPS), heat killed *B. pertussis* vaccine, and glucans. Delivery of the immunogen to the animal can utilize ISCOMS (Immune Stimulating Complexes; for example, see Coligan et al., supra), liposomes, and microparticles or similar solid phase supports.

Immunization schemes are useful for both monoclonal and polyclonal antibody production (Groves and Tucker, 1989, Vet. *Immunol. Immunpath.*, 23:1-14; Ou et al., 1991, *J. Immunol. Meth.*, 145:111-118) in normal, autoimmune, or SPF mice; rats, hamsters, guinea pigs, rabbits, ferrets, sheep, goats, or cattle, though not limited to these species. The route of administration can be subcutaneous, intramuscular, intradermal, intravenous, intraperitoneal, via the lymph system, oral, or mucosal. It can also be administered via the footpads but preferably this route is avoided because it results in undesirable distress to the animal. The doses, for example, can range from about 0.1 ug to about 10 mg depending on the weight of the animal. Sheep, mice, rabbits, or goats are preferred. Boosting frequency can range from about 1 week to about 1 year.

For example, to produce antibodies in mice, the initial immunization is with 10–20 $\mu$g of GHb/Hp complex in complete Freund's adjuvant, administered in several sites. Boosts are performed at 2–3 months using 10–20 $\mu$g GHb/Hp complex in incomplete Freund's adjuvant. To produce antibodies in rabbits, approximately 100–500 $\mu$g of GHb/Hp complex in complete Freund's adjuvant is injected. After three to four months, the animals are boosted with about 20–50 $\mu$g of antigen in incomplete Freund's adjuvant. Serum is evaluated two to three weeks later for antibodies that specifically bind GHb, GHb conformer H, Hb, and Hb conformer H antibodies. Additional boosts are administered at approximately two to three month intervals until the desired antibodies are detected in useful titer. It may also be advantageous to use human Hp complexed with GHb for the initial immunization and non-human (e.g., sheep) Hp complexed with GHb for boosts.

A strategy may be employed to induce immunologic tolerance in T and B lymphocytes (Abbas et al., 1991, *Cellular and Molecular Immunology*, W. B. Saunders Company, Philadelphia, Pa., pp. 204–221; Butler, 1991, *Immunochemistry of Solid Phase Immunoassay*, CRC Press, Boca Raton, Fla.) to exclude generation of an immune responses to any insignificant immunodominant epitopes. A few examples of tolerization techniques are through the utilization of cyclophosphamide, neonatal immunizations, and the injection of high doses of undesirable antigens.

Sera or plasma samples are taken from the animal for evaluation in immunoassays (U.S. Pat. No. 5,478,754; Goding, 1996, *Monoclonal Antibodies: Principles and Practice*, Academic Press, London, p.141–233) employing the target antigen. Suitable immunoassay formats include enzyme immunoassays (EIAs), radioimmunoassays (RIAs), fluorescent immunoassays (FIAs), electrophoretic techniques, and chemiluminescent assays in direct, indirect, or competitive inhibition assays. Preferably, screening panels include relevant cross reactants as well as the antigen of interest. Diluents containing the cross reactants can be used to absorb antibodies specific to undesirable components in the solid phase antigen assays.

Fusions use B-cells isolated fromn the spleen, peripheral blood, or lymph nodes. The EB-cells are immortalized with a compatible myeloma using standard PEG or electrofusion techniques (Goding, supra) though alternately the lymphocyte gene products may be utilized in new cell constructs or phage techniques. Cell cultures are established and cloned to ensure monoclonality with the aid of selective media. Cell banks are made to ensure the availability of an endless reagent supply. The resulting antibody (or binding agent) is tested as previously described.

Other strategies for antibody production may be used, e.g., non-murine myeloma fusions. Antibodies may also be humanized by methods known in the art.

Antibodies may be labeled with any appropriate entity including radioactive or fluorescent moieties, particulate labels (e.g., colloidal gold), or enzymes (e.g., alkaline phosphatase). Protocols for attaching labels to antibodies are known in the art.

EXAMPLES

Example 1.

Haptoglobin Binds Hemoglobin in a Dose Dependent Manner.

An ELISA format was used to demonstrate the ability of haptoglobin to bind glycated and non-glycated hemoglobin. Haptoglobin obtained from Sigma (99% pure pool of all Hp types) was resuspended in 50 mM carbonate buffer, pH 9.6 at 0.02 mg/ml. 100 µl aliquots were placed in wells of a 96-well microtiter plate and immobilized to the surface by incubation overnight at 20° C. Wells were washed 3 times with PBS/0.1% Tween 20. Wells were blocked with 50 mM glycine buffer, pH 8.0, containing 3% nonfat milk (Sigma). Hemoglobin (Pierce) or glycated hemoglobin (Pierce) were diluted to 140 µg/ml. 100 µl of hemoglobin or haptoglobin was added to Hp-coated microtiter wells and incubated for up to 20 minutes at room temperature. Wells were rinsed with PBS and antibodies against Hb (American Research Products, Inc.; ARP) and GHb (ARP) were added to the appropriate wells and incubated for 20 minutes at room temperature. Antibody binding was detected by addition of anti.-sheep antibodies conjugated to alkaline phosphatase (Sigma), diluted 1:1000 and incubated for 20 minutes at room temperature. Wells were rinsed with PBS and 200 µl of 24 mM p-nitrophenyl phosphate (p-NPP) in 0.2 M Tris buffer, pH 10.0 was added to each well. Rate of change in absorbance (was monitored at 405 nm for 10 minutes using a Labsystem Multiskan RC plate reader. Haptoglobin bound both Hb and GHb in this assay. GHb/Hb saturated Hp in less than 7.5 seconds in this experiment.

Example 2.

Hp Immobilized on Nitrocellulose Strips Binds Visually Detectable Amounts of Hb and HbA1c To assess the ability of membrane-bound Hp to bind hemoglobin and glycated hemoglobin, experiments similar to those of Example 1 were carried out. Hp was resuspended in PBS, pH 7.4 at 2.5, 1.25, 0.63, and 0.32 mg/ml and 4.0 µl of each dilution applied to nitrocellulose strips (Millipore) and dried for 1–4 hours in a drying oven at 37° C. and then stored until use. As above, Hp bound to nitrocellulose was incubated with Hb or GHb. After rinsing to remove all Hb and GHb not specifically bound to Hp, the strips were incubated with the substrate tetramethylbenzidine (TMB) for 30 seconds. TMB provides a direct measure of GHb/Hb as it is oxidized to a green chromophore by GHb/Hb oxidase activity. The resulting products were evaluated by semiquantitative visual inspection. Both GHb and Hb were detectable by this method.

Example 3.

Hb and HbA1c are Distinguishable by Different Antibodies When Bound to Hp

Figure 5:
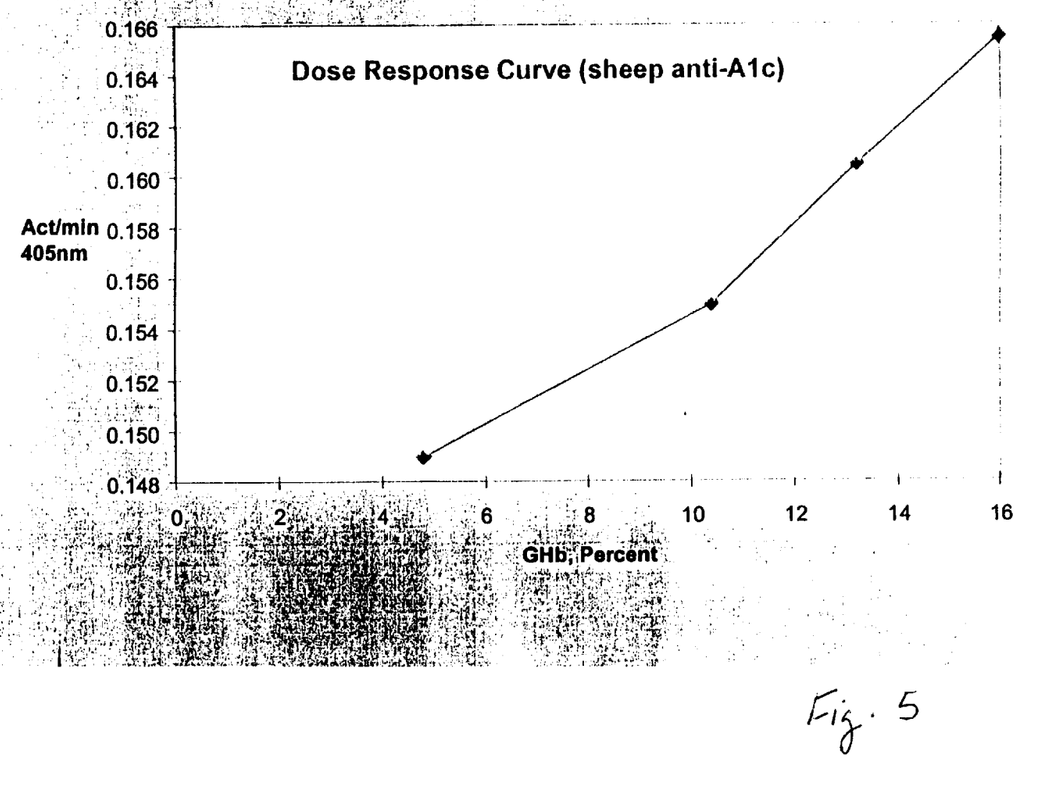
FIG. 5 is a graph of a dose-response curve detecting Hb bound to Hp using sheep anti-A1c.

Sheep anti-HbA1c polyclonal antioody was used to assay for the antigenicity of GHb when bound to Hp. Haptoglobin was immobilized in microtiter wells and saturating levels of mixtures of GHb and Hb incubated in the wells to form Hp:GHb/Hb complexes. Sheep anti-HbA1c antibodies (diluted 1:10,000) were added to the wells, incubated for 30 minutes and washed. The amount of bound antibody was detected using a secondary anti-sheep antibody conjugated to alkaline phosphatase. After washing to remove excess secondary antibody, the substrates p-NPP in Tris buffer, pH 10.0 was added. The change Ln absorbance per minute at 405 nm was monitored over 10 minutes. Samples containing normal control hemoglobin (4.8%), abnormal (diabetic) hemoglobin (16%), and mixtures of GHb and Hb containing 10.4% and 13.2% glycated hemoglobin were evaluated. As shown in FIG. 5, all four dilutions of GHb could be distinguished using this assay.

It was found that GHb/Hb saturation binding of Hp was complete in less than 7.5 seconds.

$NaBH_4$ reduces sugars on GHb to form glucitol (see WO91/02978). Because some antibodies raised against GHb recognize the glucitol form of GHb with greater specificity than native GHb, the effect of $NaBH_4$ treatment on the ability of Hp to bind treated GHb was examined.

Hp was immobilized in microtiter plates by aliquoting 2 µg/well (100 µl of 20 µg/ml in carbonate buffer, pH 9.6) and incubating overnight. The wells were washed and blocked with 3% non-fat milk in glycine buffer. Samples containing GHb and Hb (4.8%, 10.4%, 13.2%, and 16% GHb) were diluted in 50 mM $NaBH_4$ to 28 µg/ml each. 100 µl of the samples was added to wells and incubated at room temperature for 10 minutes. Wells were washed three times to remove GHb, Hb, and $NaBH_4$. Mouse anti-HbA1c was added to the wells and incubated for 30 minutes at room temperature. After washing p-NPP was added and the rate of change of absorbance measured as described above. It was found that the assay for GHb was slightly more sensitive when the glucitol (e.g. $NaBH_4$-treated) forms were used in the assay when compared to untreated forms. In this experiment, mouse monoclonal anti-GHb (Immtech), diluted 1:500, was used in place of shee(p polyclonal anti-A1C antibody. Anti-mouse IgG-conjugate was used in place of the anti-sheep IgG-alkaline phosphatase conjugate. The results were as described above.

Example 4.

Immunogen Preparation

GHb is complexed with Hp to be used as immunogen for making the antibodies described above. Hp1-1:GHb is prepared by mixing Hp1-1 (m.w.=85,000 Daltons) and GHb (m.w.=64,000 Daltons) in a ratio of 1:5, mole:mole, respectively. Each component is suspended in 50 mM PBS, pH 7.4, with costant stirring at 37° C. for 1.0 hour. This ratio insures that all active Hp1-1 binds GHb t-o form complexes. The desired yield is 20–30 mg of Hp1-1:GHb having a m.w . . . =150,000 Daltons. The mix of 30 mg of Hp1-1 and 112 mg of GHb are used as starting quantities. The GHb:Hp complex is separated from the starting materials by size exclusion gel chromatography. The purity of the complex is examined by reducing gel electrophoresis, non-reducing gel electrophoresis, and HPLC. GHb content per mg mass is determined using spectral analysis to estimate complexed Hp and GHb ratio.

Hp2-1 and Hp2-2 are larger complexes than Hp1-1, and the molecular weights vary for both pherotypes. Each has a molecular weight range that can be up to 1,000,000 Daltons or more. Excess GHb is combined with each phenotype as described above for Hp1-1 and uncomplexed GHb is removed by size exclusion chromatography. Purity eand GHb content per mg mass of GHb:Hp complex are determined as described above.

Example 5.

Use of a Gold Electrode for Detection of GHb

Figure 6:
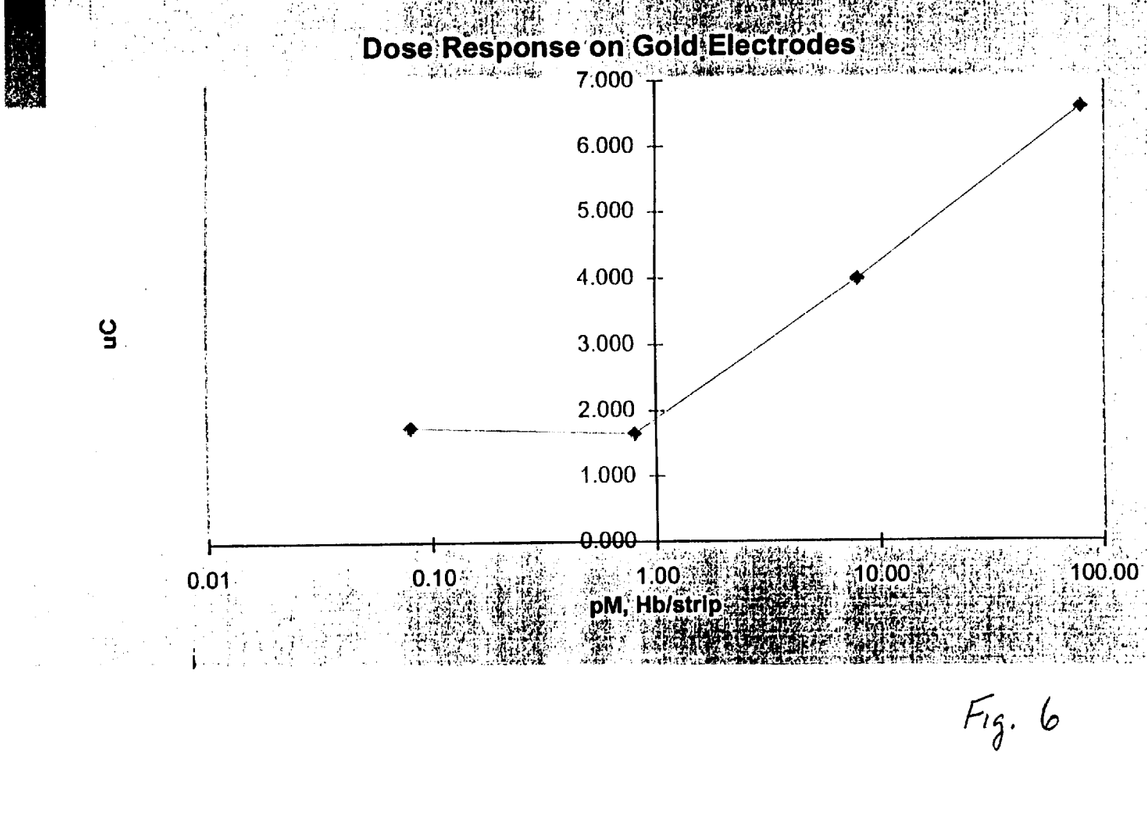
FIG. 6 is a graph of data showing the sensitivity of electrochemical methods for detecting GHb.

An experiment was performed to test the feasiblity of an assay detecting GHb bound to Hp. Hp was immobilized on a GI gold electrode strip by incubation overnight in a 20 $\mu$g/ml solution of Hp in deionized water. The electrode was washed three times with water, and storesd until use. GHb/Hb solution (2 $\mu$l of 0.0 to 5.0 nM/ml) was applied to each strip, incubated for 10 seconds, and washed three times. Strips were then incubated in the sheep anti-GHb (1:10,000) for 15 minutes, washed three times, then incubated in conjugate (1:2000), and washed. Then, 30 $\mu$l of pAPP was pipetted over the electrode surface and current measured by chronoampreometry over 30 seconds. As shown in FIG. 6, the lowest observed level of detection was approximately 1.0 pmole. Because the antibodies used in this experiment have a large amount of crossreactivity with Hb, the assay does not provide sufficient precision to be used in the invention.

We claim:

1. A method for assaying GHb in a biological fluid, if present, comprising the steps of:
   a. providing a solid support member, which member comprises a predetermined amount of a Hp,
   b. contacting said biological fluid with said support member, thereby forming a GHb/Hb-saturated support member,
   c. contacting said GHb/Hb-saturated support member with a Hb/Hp-specific probe under conditions that allow binding of said Hb/Hp-specific probe to its target, said target consisting of Hb,
   d. removing unbound Hb/Hp-specific probe, and
   e. determining the amount of said HblHp-specific probe bound to captured Hb, and calculating how much GHb is in said biological fluid, if present.

2. The method of claim 1, wherein said Hb/Hp-specific probe is an antibody.

3. The method of claim 2, wherein said antibody is selected from the group consisting of,
   a. an antibody that specifically binds Hb conformer H, and
   b. an antibody that specifically binds Hb conformer H and nondenatured Hb.

4. The method of claim 1, wherein said biological fluid is from a mammal.

5. The method of claim 4, wherein said mammal is a human.

6. The method of claim 4, wherein said mammal is a nonhuman mammal.

7. The method of claim 4, wherein said biological fluid is blood.

* * * * *

UNITED STATES PATENT AND TRADEMARK OFFICE
CERTIFICATE OF CORRECTION

PATENT NO. : 6,174,734 B1
DATED : January 16, 2001
INVENTOR(S) : Ralph K. Ito et al.

It is certified that error appears in the above-identified patent and that said Letters Patent is hereby corrected as shown below:

<u>Column 12,</u>
Line 14, replace "Hb1Hp" with -- Hb/Hp --.

Signed and Sealed this

Twenty-sixth Day of February, 2002

Attest:

Attesting Officer

JAMES E. ROGAN
Director of the United States Patent and Trademark Office